(12) United States Patent
Mahe et al.

(10) Patent No.: US 8,771,659 B2
(45) Date of Patent: Jul. 8, 2014

(54) COSMETIC COMPOSITIONS COMPRISING AT LEAST ONE STARCH AND AT LEAST ONE PEG FATTY DIESTER, AND USES THEREOF

(75) Inventors: Véronique Mahe, Vaux S/Seine (FR); Jean-Michel Sturla, Boulogne (FR)

(73) Assignee: L'Oreal, Paris (FR)

( * ) Notice: Subject to any disclaimer, the term of this patent is extended or adjusted under 35 U.S.C. 154(b) by 576 days.

(21) Appl. No.: 11/822,033

(22) Filed: Jul. 2, 2007

(65) Prior Publication Data

US 2008/0152605 A1 Jun. 26, 2008

Related U.S. Application Data

(60) Provisional application No. 60/819,372, filed on Jul. 10, 2006.

(30) Foreign Application Priority Data

Jun. 30, 2006 (FR) .................................... 06 52730

(51) Int. Cl.
*A61K 8/60* (2006.01)
*A61K 47/26* (2006.01)
*A61Q 5/12* (2006.01)
*A61Q 5/00* (2006.01)

(52) U.S. Cl.
USPC ............ 424/70.2; 424/62; 424/70.1; 514/778

(58) Field of Classification Search
USPC ....................................................... 424/70.2
See application file for complete search history.

(56) References Cited

U.S. PATENT DOCUMENTS

| | | |
|---|---|---|
| 4,017,460 A | 4/1977 | Tessler |
| 4,217,914 A | 8/1980 | Jacquet et al. |
| 4,240,450 A | 12/1980 | Grollier et al. |
| 4,422,853 A | 12/1983 | Jacquet et al. |
| 4,445,521 A | 5/1984 | Grollier et al. |
| 4,693,935 A | 9/1987 | Mazurek |
| 4,719,099 A | 1/1988 | Grollier et al. |
| 4,728,571 A | 3/1988 | Clemens et al. |
| 4,839,166 A | 6/1989 | Grollier et al. |
| 4,948,579 A | 8/1990 | Jacquet et al. |
| 4,957,732 A | 9/1990 | Grollier et al. |
| 4,972,037 A | 11/1990 | Garbe et al. |
| 4,996,059 A | 2/1991 | Grollier et al. |
| 5,009,880 A | 4/1991 | Grollier et al. |
| 5,089,252 A | 2/1992 | Grollier et al. |
| 5,139,037 A | 8/1992 | Grollier et al. |
| 5,196,189 A | 3/1993 | Jacquet et al. |
| 5,455,340 A | 10/1995 | Bernard et al. |
| 5,958,392 A | 9/1999 | Grollier et al. |
| 5,968,492 A * | 10/1999 | Noguchi et al. ............. 424/70.1 |
| 6,153,208 A * | 11/2000 | McAtee et al. ............... 424/402 |
| 6,166,093 A | 12/2000 | Mougin et al. |
| 6,319,959 B1 | 11/2001 | Mougin et al. |
| 7,541,320 B2 * | 6/2009 | Dabkowski et al. .......... 510/122 |
| 2003/0181744 A1 * | 9/2003 | Pereira et al. ................. 554/228 |
| 2005/0069511 A1 * | 3/2005 | Magnet et al. ............. 424/70.13 |
| 2005/0164896 A1 | 7/2005 | Dabkowski et al. |

FOREIGN PATENT DOCUMENTS

| | | |
|---|---|---|
| DE | 102 10 461 A1 | 9/2003 |
| EP | 0 342 834 B1 | 11/1989 |
| EP | 0 412 704 B1 | 2/1991 |
| EP | 0 412 707 B1 | 2/1991 |
| EP | 0 582 152 B1 | 2/1994 |
| EP | 0 619 111 B1 | 10/1994 |
| EP | 0 751 162 B1 | 1/1997 |
| EP | 1 051 967 A2 | 11/2000 |
| EP | 1 389 459 A1 | 2/2004 |
| FR | 2 270 846 | 12/1975 |
| FR | 2 383 660 | 10/1978 |
| FR | 2 470 596 | 6/1981 |
| FR | 2 519 863 | 7/1983 |
| FR | 2 589 476 A1 | 5/1987 |
| FR | 2 598 611 A1 | 11/1987 |
| FR | 2 824 733 A1 | 11/2002 |
| WO | WO 93/23009 | 11/1993 |
| WO | WO 93/23446 | 11/1993 |
| WO | WO 95/00578 | 1/1995 |
| WO | WO 98/01109 A1 | 1/1998 |
| WO | WO 03/084486 A1 | 10/2003 |
| WO | WO 03/084488 A1 | 10/2003 |
| WO | WO 2006/136332 A1 | 12/2006 |

OTHER PUBLICATIONS

French Search Report for FR 0652730, dated Jan. 26, 2007.
Charles Todd et al., "Volatile silicone fluids for cosmetic formulations," Cosmetics and Toiletries, vol. 91, pp. 29-32 (1976).
M.R. Porter, BSc, PhD, CChem, MRSC, "Handbook of Surfactants," Blackie & Son, Ltd., Glasgow and London, pp. 116-178 (1991).
English language abstract of DE 102 10 461 A1, Sep. 18, 2003.
English language abstract of EP 1 051 967 A2, Nov. 15, 2000.
English language abstract of FR 2 589 476 A1, May 7, 1987.

(Continued)

*Primary Examiner* — Janet Epps-Smith
*Assistant Examiner* — Audrea Buckley
(74) *Attorney, Agent, or Firm* — The Marbury Law Group, PLLC.

(57) ABSTRACT

The present disclosure relates to novel cosmetic compositions comprising, in a cosmetically acceptable aqueous medium:

from 0.1% to 2% by weight of at least one starch, and
from 0.1% to 1% by weight, relative to the total weight of the composition, of at least one diester of a carboxylic acid comprising 8 to 30 carbon atoms and of polyethylene glycol. The cosmetic compositions provides a fondant texture, and these compositions rinse out easily. Hair treated with this composition has a soft feel, free of residue. These compositions are may be used for washing and/or conditioning keratin materials such as the hair or the skin.

20 Claims, No Drawings

(56) References Cited

OTHER PUBLICATIONS

"Structure® XL (28-030A) Hydroxylpropyl Starch Phosphate," National Starch (Jul. 2002).

"Dry-Flo® Pure (28-1850 US) & Dry-Flo® Plus (28-1160 EU), Aluminum Starch Octenylsuccinate," National Starch (Dec. 2001).

* cited by examiner

COSMETIC COMPOSITIONS COMPRISING AT LEAST ONE STARCH AND AT LEAST ONE PEG FATTY DIESTER, AND USES THEREOF

This application claims benefit of U.S. Provisional Application No. 60/819,372, filed Jul. 10, 2006, the contents of which are incorporated herein by reference. This application also claims benefit of priority under 35 U.S.C. §119 to French Patent Application No. FR 06 52730, filed Jun. 30, 2006, the contents of which are also incorporated herein by reference.

The present disclosure relates to novel cosmetic compositions comprising, in a cosmetically acceptable medium, at least one particular carboxylic acid ester and at least one starch.

It is known that hair that has been sensitized (i.e., damaged and/or embrittled) to varying degrees under the action of atmospheric agents or under the action of mechanical or chemical treatments, such as dyeing, bleaching and/or permanent-waving, is often difficult to disentangle and to style, and lacks softness.

Cosmetic compositions comprising thickening polysaccharides, such as starch or celluloses, have already been proposed for treating keratin materials, such as the hair.

However, such compositions may have drawbacks such as rinseability problems, problems of stability at acidic pH, difficulties in spreading on keratin materials, and also insufficient cosmetic properties.

Hair care products that are desired by users are those that can be measured out and taken up easily in the hand. To do this, these products should have a certain consistency. Specifically, a liquid product is much more difficult to measure out and flows easily between the fingers. On the other hand, it is easier to apply to the hair and spreads uniformly. Unfortunately, thick products are generally difficult to spread on the hair and may give the head of hair non-uniform care. Furthermore, whether they are thick or liquid, the products may not lead to the perception of a sufficient treating effect.

To summarize, it turns out that the current cosmetic compositions are not always entirely satisfactory.

The present inventors have now discovered, surprisingly, that the combination of at least one starch with at least one carboxylic ester allows at least one of these drawbacks to be overcome.

Thus, after considerable research conducted in this matter, the present inventors have now found that the use of compositions, such as hair compositions, based on particular esters and on starch can limit or even eliminate at least one of the problems outlined above.

This combination may give the cosmetic compositions a fondant texture. The compositions may spread quickly and easily throughout the head of hair, while at the same time remaining on the surface of the hair. Moreover, they are also typically very easy to rinse out.

Hair treated with this composition may disentangle easily, have a soft feel, free of residue, and/or be smooth from the root to the end, and the style hold may be improved.

The compositions of the present disclosure may also have a good treating effect, which, when combined with the good texture and/or spreading properties of the product, can give the user a sensation of deep-down care.

It has already been proposed in French Patent No. 2 824 733 to combine starches with liquid fatty esters, but the compositions obtained therein do not always have good working qualities. For example, the ease of spreading of the product and the treating effect perceived are often still unsatisfactory.

Moreover, when the compositions of the present disclosure are applied to the skin, for instance, in the form of a bubble bath or a shower gel, they may provide an improvement in the softness of the skin.

Thus, according to the present disclosure, novel cosmetic compositions are now proposed, comprising, in a cosmetically acceptable aqueous medium:

from 0.1% to 2% by weight, relative to the total weight of the composition, of at least one starch, and from 0.1% to 1% by weight, relative to the total weight of the composition, of at least one diester of a carboxylic acid comprising 8 to 30 carbon atoms and of polyethylene glycol, the diester comprising 80 to 350 mol of ethylene oxide.

Another embodiment of the present disclosure concerns the use of starch in or for the manufacture of a cosmetic composition comprising a diester as defined herein.

Another embodiment of the present disclosure concerns a process for conditioning keratin fibers, for example the hair, comprising applying the cosmetic composition as defined herein.

Another embodiment of the present disclosure concerns a process for treating and/or conditioning keratin fibers, for example the hair, comprising applying a cosmetic composition comprising, in a cosmetically acceptable medium:

from 0.1% to 2% by weight, relative to the total weight of the composition, of at least one starch, and from 0.1% to 1% by weight, relative to the total weight of the composition, of at least one diester of a carboxylic acid comprising 8 to 30 carbon atoms and of polyethylene glycol.

The various subjects, characteristics, and aspects of the present disclosure will be detailed in the description and various examples that follow. All the meanings and definitions of the compounds used in the present disclosure given below are valid for all of the aspects of the disclosure.

The starches that may be used herein are, for example, macromolecules in the form of polymers comprising elementary units, which are anhydroglucose units. The number of these units and their assembly make it possible to distinguish amylose (linear polymer) and amylopectin (branched polymer). The relative proportions of amylose and of amylopectin, and also their degree of polymerization, vary as a function of the botanical origin of the starches.

The botanical origin of the starch molecules used in the present disclosure may be cereals or tubers. Thus, the starches may be chosen, for example, from corn starch, rice starch, cassava starch, oat starch, tapioca starch, barley starch, potato starch, wheat starch, sorghum starch, and pea starch.

Hydrolysates of the starches mentioned above may also be used in at least one embodiment of the present disclosure. In at least one embodiment, the starch is derived from potato.

The starches may be in the form of a white powder, which is insoluble in cold water, the size of the elementary particles of which ranges from 3 to 100 microns The starches used in the composition may be modified by at least one of the following reactions: pregelatinization, oxidation, crosslinking, esterification, and heat treatments.

These reactions may be performed, for example, in the following manner:

pregelatinization by splitting the starch granules (for example drying and cooking in a drying drum);

oxidation with strong oxidizing agents, leading to the introduction of carboxyl groups into the starch molecule and to depolymerization of the starch molecule (for example by treating an aqueous starch solution with sodium hypochlorite);

crosslinking with functional agents capable of reacting with the hydroxyl groups of the starch molecules, which will thus bond together (for example with glyceryl and/or phosphate groups);

esterification in alkaline medium for the grafting of functional groups, such as $C_1$-$C_6$ acyl (acetyl), $C_1$-$C_6$ hydroxyalkyl (hydroxyethyl or hydroxypropyl), carboxymethyl or octenylsuccinic.

Monostarch phosphates (of the type Am—O—PO—(OX)$_2$), distarch phosphates (of the type Am—O—PO—(OX)—O—Am) or even tristarch phosphates (of the type Am—O—PO—(O—Am)$_2$) or mixtures thereof may, for example, be obtained by crosslinking with phosphorus compounds.

X is chosen from, in at least one embodiment, alkali metals, for example sodium or potassium, alkaline-earth metals, for example calcium or magnesium, ammonium salts, amine salts, for instance those of monoethanolamine, diethanolamine, triethanolamine, 3-amino-1,2-propanediol, and ammonium salts derived from basic amino acids such as lysine, arginine, sarcosine, ornithine or citrulline.

The phosphorus compounds may be, for example, sodium tripolyphosphate, sodium orthophosphate, phosphorus oxychloride or sodium trimetaphosphate.

Distarch phosphates or compounds rich in distarch phosphate may be used, for instance, the products sold under the trade names PREJEL VA-70-T AGGL (gelatinized hydroxypropyl cassava distarch phosphate), PREJEL TK1 (gelatinized cassava distarch phosphate) and PREJEL 200 (gelatinized acetyl cassava distarch phosphate) by the company Avebe, or STRUCTURE ZEA from National Starch (gelatinized corn distarch phosphate).

In at least one embodiment of the present disclosure, amphoteric starches may also be used, such amphoteric starches comprising at least one anionic group and at least one cationic group. The anionic and cationic groups may be linked to the same reactive site of the starch molecule or to different reactive sites; in at least one embodiment they may be linked to the same reactive site. The anionic groups may be of carboxylic, phosphate, or sulfate type, and in at least one embodiment are carboxylic. The cationic groups may be of primary, secondary, tertiary, or quaternary amine type.

The amphoteric starches may, for example, be chosen from compounds having the following formulae:

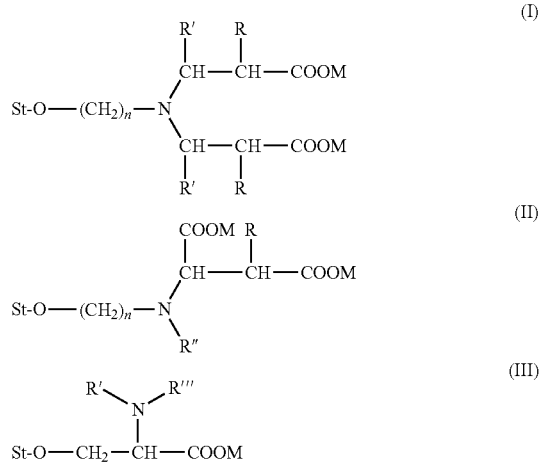

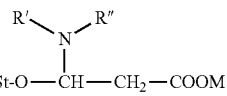

wherein formulae:
St-O is a starch molecule,
R, which may be identical or different, is chosen from hydrogen and methyl radicals,
R', which may be identical or different, is chosen from hydrogen, methyl radicals, and —COOH groups,
n is an integer equal to 2 or 3,
M, which may be identical or different, is chosen from hydrogen, alkali metals, or alkaline-earth metals such as Na, K, $L_1$ or $NH_4$, a quaternary ammonium, and an organic amine,
R" is chosen from hydrogen and alkyl radicals comprising 1 to 18 carbon atoms.

These compounds are, for instance, described in U.S. Pat. Nos. 5,455,340 and 4,017,460, which are hereby incorporated by reference.

In at least one embodiment, starches of formula (I) or (II) are used. Starches modified with 2-chloroethylaminodipropionic acid may, for example, be used, i.e., starches of formula (I) or (II) wherein R, R', R" and M are all chosen from hydrogen and n is equal to 2.

The starches may be, for example, used in an amount ranging from 0.1% to 1% by weight relative to the total weight of the composition.

The diesters of a carboxylic acid comprising 8 to 30 carbon atoms and of polyethylene glycol comprise 80 to 350 mol of ethylene oxide (EO).

The diesters of a carboxylic acid comprising 8 to 30 carbon atoms and of polyethylene glycol have the following formula:

$$R_1\text{—CO(O—CH}_2\text{—CH}_2)_n\text{—OOCR}_2 \qquad (I)$$

wherein:
$R_1$ is chosen from linear or branched, saturated or unsaturated alkyl and alkenyl groups comprising 8 to 30 carbon atoms; in at least one embodiment, $R_1$ is a linear alkyl group comprising 12 to 20 carbon atoms.
$R_2$ is chosen from linear or branched and saturated or unsaturated alkyl groups comprising 8 to 30 carbon atoms; in at least one embodiment, $R_2$ is a linear alkyl group comprising 12 to 20 carbon atoms.
n is an integer ranging from 80 to 350, for example, from 100 to 300.

In at least one embodiment, the weight ratio of the hydrophilic portion (—(O—CH$_2$—CH$_2$)nO) to the hydrophobic portion ($R_1$ and $R_2$) ranges from 8 to 1000.

In at least one embodiment, a compound of formula (I) wherein $R_1$ and $R_2$ are each independently chosen from linear alkyl groups comprising 12 to 20 carbon atoms, for example, comprising 16 to 20 carbon atoms, and n ranges from 100 to 300 may be used. Non-limiting examples that may be mentioned include PEG 150 distearate (n=150) and PEG 250 distearate (n=250).

Such compounds are sold under the name EMANON 3299R by the company Kao and under the name KESSCO PEG 6000 DS by the company Akzo.

The diesters of a carboxylic acid and of PEG may be present in an amount ranging from 0.1% to 0.5% by weight relative to the total weight of the final composition.

According to one embodiment of the present disclosure, the compositions, as disclosed herein, also comprise at least one agent that is beneficial for the hair, such as silicones, plant, animal, mineral or synthetic oils, waxes, ceramides, pseudoceramides, cationic polymers, surfactants, for example cationic surfactants, fatty esters other than those of the disclosure, sunscreens and vitamins, and mixtures thereof.

The silicones that may be used in accordance with the present disclosure are, for instance, polyorganosiloxanes that are insoluble in the composition and that may be in the form of oils, waxes, resins or gums.

The organopolysiloxanes are, for example, defined in greater detail in Walter Noll's "Chemistry and Technology of Silicones" (1968) Academic Press. They can be volatile or non-volatile.

When they are volatile, the silicones may be, for instance, chosen from those having a boiling point ranging from 60° C. to 260° C., and, further for example, from:

(i) cyclic silicones comprising 3 to 7 and, for example, from 4 to 5 silicon atoms.

These are, for example, octamethylcyclotetrasiloxane sold under the trade names VOLATILE SILICONE 7207 by Union Carbide or SILBIONE 70045 V 2 by Rhône-Poulenc, decamethylcyclopentasiloxane sold under the name VOLATILE SILICONE 7158 by Union Carbide, and SILBIONE 70045 V 5 by Rhône-Poulenc, and mixtures thereof.

Non-limiting mention may also be made of cyclocopolymers of the dimethylsiloxanes/methylalkylsiloxane type, such as VOLATILE SILICONE FZ 3109 sold by the company Union Carbide, having the chemical structure:

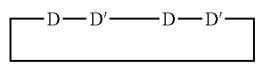

with D:

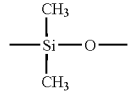

with D':

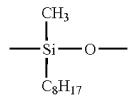

Non-limiting mention may also be made of mixtures of cyclic silicones with organosilicon compounds, such as the mixture of octamethylcyclotetrasiloxane and tetratrimethylsilylpentaerythritol (50/50) and the mixture of octamethylcyclotetrasiloxane and oxy-1,1'-bis(2,2,2',2',3,3'-hexatrimethylsilyloxy)neopentane;

(ii) linear volatile silicones comprising from 2 to 9 silicon atoms and having a viscosity of less than or equal to $5 \times 10^{-6}$ m²/s at 25° C.

An example is decamethyltetrasiloxane sold under the name SH 200 by the company Toray Silicone. Silicones belonging to this category are also described in the article published in Cosmetics and Toiletries, Vol. 91, January 76, pp. 27-32, Todd & Byers "Volatile Silicone Fluids for Cosmetics".

Non-volatile silicones and, for example, polyalkylsiloxanes, polyarylsiloxanes, polyalkylarylsiloxanes, silicone gums and resins, polyorganosiloxanes modified with organofunctional groups, and mixtures thereof, may be used in at least one embodiment of the present disclosure.

These silicones may be chosen from polyalkylsiloxanes, among which non-limiting mention may be made mainly of polydimethylsiloxanes comprising trimethylsilyl end groups having a viscosity from $5 \times 10^{-6}$ to 2.5 m²/s at 25° C. and, for example, $1 \times 10^{-5}$ to 1 m²/s. The viscosity of the silicones is measured, for example, at 25° C. according to ASTM standard 445 Appendix C.

Among these polyalkylsiloxanes, non-limiting mention may be made of the following commercial products:

the Silbione oils of the 47 and 70 047 series or the Mirasil oils sold by Rhône-Poulenc, such as, for example, the oil 70 047 V 500 000;

the oils of the Mirasil series sold by the company Rhône-Poulenc;

the oils of the 200 series from the company Dow Corning, such as, DC200 with a viscosity of 60 000 cSt;

the Viscasil oils from General Electric and certain oils of the SF series (SF 96, SF 18) from General Electric.

Non-limiting mention may also be made of polydimethylsiloxanes comprising dimethylsilanol end groups (Dimethiconol according to the CTFA name) such as the oils of the 48 series from the company Rhône-Poulenc.

In this category of polyalkylsiloxanes, non-limiting mention may also be made of the products sold under the names ABIL WAX 9800 and 9801 by the company Goldschmidt, which are poly($C_1$-$C_{20}$)alkylsiloxanes.

The polyalkylarylsiloxanes are chosen, for example, from linear and/or branched polydimethylmethylphenylsiloxanes and polydimethyldiphenylsiloxanes with a viscosity from $1 \times 10^{-5}$ to $5 \times 10^{-2}$ m²/s at 25° C.

Among these polyalkylarylsiloxanes, non-limiting mention may be made, by way of example, of the products sold under the following names:

the Silbione oils of the 70 641 series from Rhône-Poulenc;

the oils of the Rhodorsil 70 633 and 763 series from Rhône-Poulenc;

the oil Dow Corning 556 Cosmetic Grade Fluid from Dow Corning;

the silicones of the PK series from Bayer, such as the product PK20;

the silicones of the PN and PH series from Bayer, such as the products PN1000 and PH1000;

certain oils of the SF series from General Electric, such as SF 1023, SF 1154, SF 1250 and SF 1265.

The silicone gums that can be used in accordance with the present disclosure are, for instance, polydiorganosiloxanes with high number-average molecular masses ranging from 200 000 to 1 000 000, used alone or as a mixture in a solvent. This solvent can be chosen from volatile silicones, polydimethylsiloxane (PDMS) oils, polyphenyl-methylsiloxane (PPMS) oils, isoparaffins, polyisobutylenes, methylene chloride, pentane, dodecane and tridecane, and mixtures thereof.

Non-limiting mention may be made of the following products:

polydimethylsiloxane, polydimethylsiloxane/methylvinylsiloxane gums, polydimethylsiloxane/diphenylsiloxane, polydimethylsiloxane/phenylmethylsiloxane, and polydimethylsiloxane/diphenylsiloxane/methylvinylsiloxane.

Non-limiting examples of products that can be used in accordance with the present disclosure are mixtures such as:

mixtures formed from a polydimethylsiloxane hydroxylated at the chain end (referred to as dimethiconol according to the nomenclature in the CTFA dictionary) and from a cyclic polydimethylsiloxane (referred to as cyclomethicone according to the nomenclature in the CTFA dictionary), such as the product Q2 1401 sold by the company Dow Corning;

mixtures formed from a polydimethylsiloxane gum with a cyclic silicone, such as the product SF 1214 Silicone Fluid from the company General Electric; this product is an SF 30 gum corresponding to a dimethicone, having a number-average molecular weight of 500 000, dissolved in the oil SF 1202 Silicone Fluid corresponding to decamethylcyclopentasiloxane;

mixtures of two PDMSs with different viscosities and, for example, of a PDMS gum and a PDMS oil, such as the product SF 1236 from the company General Electric. The product SF 1236 is a mixture of an SE 30 gum defined above, having a viscosity of 20 m²/s, and an SF 96 oil, with a viscosity of 5×10⁻⁶ m²/s. This product may comprise 15% SE 30 gum and 85% SF 96 oil.

The organopolysiloxane resins that can be used in accordance with the present disclosure are crosslinked siloxane systems comprising the following units:

$R_2SiO_{2/2}$, $R_3SiO_{1/2}$, $RSiO_{3/2}$ and $SiO_{4/2}$ wherein R is chosen from hydrocarbon-based groups comprising 1 to 16 carbon atoms or phenyl groups. Among these products, R may be chosen from, for instance, $C_1$-$C_4$ lower alkyl radicals, such as methyl or a phenyl radical.

Among these resins, non-limiting mention may be made of the product sold under the name Dow Corning 593 or those sold under the names SILICONE FLUID SS 4230 and SS 4267 by the company General Electric, which are silicones of dimethyl/trimethyl siloxane structure.

Non-limiting mention may also be made of the trimethyl siloxysilicate type resins sold, for example, under the trade names X22-4914, X21-5034 and X21-5037 by the company Shin-Etsu.

In one embodiment of the present disclosure, the organomodified silicones that can be used in accordance with the present disclosure are silicones, as defined herein, and comprising in their structure at least one organofunctional group attached via a hydrocarbon-based radical.

Among the organomodified silicones, non-limiting mention may be made of polyorganosiloxanes comprising:

polyethyleneoxy and/or polypropyleneoxy groups optionally comprising $C_6$-$C_{24}$ alkyl groups, such as the products known as dimethicone copolyol sold by the company Dow Corning under the name DC 1248 or the oils SILWET L 722, L 7500, L 77 and L 711 by the company Union Carbide, and the ($C_{12}$)alkylmethicone copolyol sold by the company Dow Corning under the name Q2 5200;

substituted or unsubstituted amine groups, such as the products sold under the name GP 4 Silicone Fluid and GP 7100 by the company Genesee, or the products sold under the names Q2 8220 and Dow Corning 929 or 939 by the company Dow Corning. The substituted amine groups are, for example, $C_1$-$C_4$ aminoalkyl groups;

thiol groups such as the products sold under the names GP 72 A and GP 71 from Genesee;

alkoxylated groups such as the product sold under the name SILICONE COPOLYMER F-755 by SWS Silicones and ABIL WAX 2428, 2434 and 2440 by the company Goldschmidt;

hydroxylated groups such as the polyorganosiloxanes comprising a hydroxyalkyl function, described, for example, in French Patent Application FR-A-85/16334, published as FR 2 589 476.

corresponding to formula (IX):

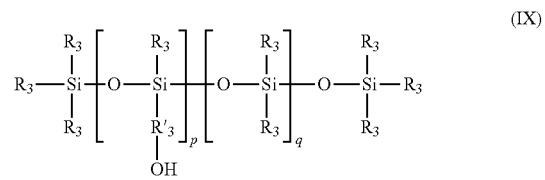

wherein:
the radicals $R_3$, which may be identical or different, are chosen from methyl and phenyl radicals; at least 60 mol % of the radicals $R_3$ are methyl; the radical $R_{13}$ is a $C_2$-$C_{18}$ divalent hydrocarbon-based alkylene chain unit; p ranges from 1 to 30 inclusive; q ranges from 1 to 150 inclusive;

acyloxyalkyl groups such as, for example, the polyorganosiloxanes described in U.S. Pat. No. 4,957,732 and corresponding to formula (X):

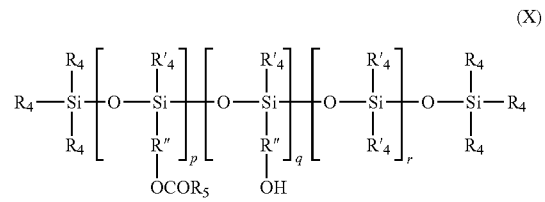

wherein:
$R_4$ is chosen from methyl, phenyl, —$OCOR_5$ and hydroxyl groups, only one of the radicals $R_4$ per silicon atom possibly being OH;
$R'_4$ is chosen from methyl and phenyl; at least 60 mol % of all the radicals $R_4$ and $R'_4$ are methyl;
$R_5$ are chosen from $C_8$-$C_{20}$ alkyl or alkenyl;
R" are chosen from $C_2$-$C_{18}$ linear or branched divalent hydrocarbon-based alkylene radicals;
r ranges from 1 to 120 inclusive;
p ranges from 1 to 30;
q is equal to 0 or is less than 0.5 p, p+q ranges from 1 to 30; the polyorganosiloxanes of formula (VI) may comprise groups:

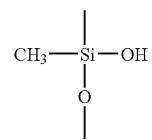

in proportions not exceeding 15% of the sum p+q+r;
anionic groups of carboxylic type, for example, in the products described in European Patent No. EP 186 507 from the company Chisso Corporation, or of alkylcarboxylic type, such as those present in the product X-22-3701 E from the company Shin-Etsu; 2-hydroxyalkyl sulfonate; 2-hydroxyalkyl thiosulfate such as the products sold by the company Goldschmidt under the names ABIL S201 and ABIL S255;

hydroxyacylamino groups, such as the polyorganosiloxanes described, for example, in European Patent No. EP 342 834. Non-limiting mention may be made, for example, of the product Q2-8413 from the company Dow Corning.

According to at least one embodiment of the present disclosure, it is also possible to use silicones comprising a polysiloxane portion and a portion comprising a non-silicone organic chain, one of the two portions constituting the main chain of the polymer, the other being grafted onto the said main chain. These polymers are described, for example, in European Patent Application Nos. EP-A-412 704, EP-A-412 707, EP-A-640 105, International Patent No. WO 95/00578, European Patent Application No. EP-A-582 152, International Patent No. WO 93/23009 and U.S. Pat. Nos. 4,693,935, 4,728,571 and 4,972,037. In at least one embodiment, these polymers are anionic or nonionic.

Such polymers are, for example, copolymers that can be obtained by free-radical polymerization starting with a monomer mixture comprising:
a) 50% to 90% by weight of tert-butyl acrylate;
b) 0 to 40% by weight of acrylic acid;
c) 5% to 40% by weight of silicone macromer of formula:

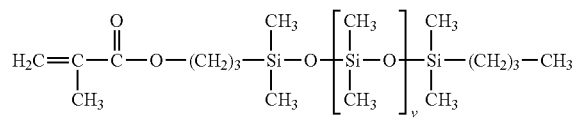

with v being a number ranging from 5 to 700; the weight percentages being calculated relative to the total weight of the monomers.

Other non-limiting examples of grafted silicone polymers are polydimethylsiloxanes (PDMS) onto which are grafted, via a connecting chain unit of thiopropylene type, mixed polymer units of poly(meth)acrylic acid type and of polyalkyl (meth)acrylate type and polydimethylsiloxanes (PDMS) onto which are grafted, via a connecting chain unit of thiopropylene type, polymer units of polyisobutyl(meth)acrylate type.

According to another embodiment of the present disclosure, it is also possible to use silicone polyurethanes, such as those described, for instance, in European Patent Application Nos. EP 0 751 162 and EP 0 619 111.

According to the present disclosure, all of the silicones can also be used in the form of emulsions, nanoemulsions, or microemulsions.

Non-limiting examples of the polyorganosiloxanes that may be used in accordance with the present disclosure are:

non-volatile silicones chosen from the family of polyalkylsiloxanes comprising trimethylsilyl end groups, such as oils having a viscosity ranging from 0.2 to 2.5 m$^2$/s at 25° C., such as the oils of the DC200 series from Dow Corning, for example those with a viscosity of 60 000 cSt, of the SILBIONE 70047 and 47 series and, for example, the oil 70 047 V 500 000, which are sold by the company Rhône-Poulenc, polyalkylsiloxanes comprising dimethylsilanol end groups, such as dimethiconols, or polyalkylarylsiloxanes such as the oil SILBIONE 70641 V 200 sold by the company Rhône-Poulenc;

the organopolysiloxane resin sold under the name Dow Corning 593;

polysiloxanes comprising amine groups, such as amodimethicones or trimethylsilyl amodimethicones.

The cationic polymers that may be used in accordance with the present disclosure may be chosen from all those already known per se as improving the cosmetic properties of the hair, for example, those described in European Patent Application EP-A0 337 354 and in French Patent Applications FR-A-2 270 846, 2 383 660, 2 598 611, 2 470 596, and 2 519 863.

As used herein, the term "cationic polymer" is understood to mean any polymer comprising cationic groups and/or groups that may be ionized into cationic groups.

In at one embodiment of the present disclosure, the cationic polymers that may be used are chosen from units comprising primary, secondary, tertiary and/or quaternary amine groups that either may form part of the main polymer chain or may be borne by a side substituent directly attached thereto.

The cationic polymers used may have a number-average molecular mass ranging from 500 and $5 \times 10^6$ and, for example, from $10^3$ to $3 \times 10^6$.

Non-limiting mention may be made among the cationic polymers of polymers of the polyamine, polyamino amide, and polyquaternary ammonium type. These are known products.

Among all the cationic polymers that may be used herein, at least one embodiment of the present disclosure may use quaternary cellulose ether derivatives such as the products sold under the name JR 400 by the company Union Carbide Corporation, cationic cyclopolymers, for example, the dimethyldiallylammonium chloride homopolymers or copolymers sold under the names Merquat® 100, Merquat® 550 and Merquat® S by the company Calgon, quaternary polymers of vinylpyrrolidone and of vinylimidazole, and crosslinked homopolymers or copolymers of methacryloyloxy($C_1$-$C_4$) alkyltri($C_1$-$C_4$)alkylammonium salts, and mixtures thereof.

According to the present disclosure, the additional beneficial agents may be present in an amount ranging from 0.001% to 20% by weight, for example from 0.01% to 10% by weight and, further for example, from 0.1% to 5% by weight relative to the total weight of the final composition.

In one embodiment of the present disclosure, the compositions, as disclosed herein, also comprise at least one surfactant, which may be present in an amount ranging from 0.01% to 50% by weight approximately, for instance from 0.1% to 40% and further for example from 0.5% to 30% by weight, relative to the total weight of the composition.

This surfactant may be chosen from anionic, amphoteric, nonionic and cationic surfactants, and mixtures thereof.

The surfactants that are suitable for use in the present disclosure include the following:
(i) Anionic Surfactant(s):

In the context of the present disclosure, their nature does not represent a truly critical factor. Thus, as examples of anionic surfactants which can be used, alone or as mixtures, in the context of the present disclosure, non-limiting mention may be made of salts (for example alkaline salts, such as sodium salts, ammonium salts, amine salts, amino alcohol salts or magnesium salts) of the following compounds: alkyl sulfates, alkyl ether sulfates, alkylamido ether sulfates, alkylarylpolyether sulfates, monoglyceride sulfates; alkyl sulfonates, alkyl phosphates, alkylamide sulfonates, alkylaryl sulfonates, α-olefin sulfonates, paraffin sulfonates; alkyl sulfosuccinates, alkyl ether sulfosuccinates, alkylamide sulfosuccinates; alkyl sulfosuccinamates; alkyl sulfoacetates; alkyl ether phosphates; acyl sarcosinates; acyl isethionates and N-acyltaurates, the alkyl or acyl radical of all of these various compounds, for example, comprising 8 to 24 carbon atoms, and the aryl radical, for instance, chosen from phenyl and benzyl groups. Among the anionic surfactants which can also be used, non-limiting mention may also be made of fatty acid salts such as the salts of oleic, ricinoleic, palmitic and stearic acids, coconut oil acid or hydrogenated coconut oil acid; acyl lactylates wherein the acyl radical comprise 8 to 20 carbon atoms. Weakly anionic surfactants can also be used, such as alkyl-D-galactosiduronic acids and salts thereof, and also polyoxyalkylenated (C6-C24)alkyl ether carboxylic acids, polyoxyalkylenated (C6-C24)alkylaryl ether carboxylic acids and polyoxyalkylenated (C6-C24)alkylamido ether carboxylic acids, and salts thereof, for instance, those comprising from 2 to 50 ethylene oxide groups, and mixtures thereof.

Among the anionic surfactants, the salts of alkyl sulfates and alkyl ether sulfates, and mixtures thereof, may be used in at least one embodiment.

(ii) Nonionic Surfactant(s):

The nonionic surfactants may be, themselves also, compounds that are well known per se (see, for instance, in this respect "Handbook of Surfactants" by M. R. Porter, published by Blackie & Son (Glasgow and London), 1991, pp. 116-178) and, in the context of the present disclosure, their nature is not a critical feature. Thus, non-limiting examples of nonionic surfactants include polyethoxylated, polypropoxylated or polyglycerolated fatty acids, alkylphenols, α-diols or alcohols comprising a fatty chain comprising, for example, 8 to 18 carbon atoms, it being possible for the number of ethylene oxide or propylene oxide groups to range, for example, from 2 to 50 and for the number of glycerol groups to range, for instance, from 2 to 30. Non-limiting mention may also be made of copolymers of ethylene oxide and of propylene oxide, condensates of ethylene oxide and of propylene oxide with fatty alcohols; polyethoxylated fatty amides, for example, comprising from 2 to 30 mol of ethylene oxide, polyglycerolated fatty amides comprising on average from 1 to 5, and, for example, 1.5 to 4 glycerol groups; polyethoxylated fatty amines, for instance, comprising 2 to 30 mol of ethylene oxide; oxyethylenated fatty acid esters of sorbitan comprising from 2 to 30 mol of ethylene oxide; fatty acid esters of sucrose, fatty acid esters of polyethylene glycol, alkylpolyglycosides, N-alkylglucamine derivatives, amine oxides such as ($C_{10}$-$C_{14}$)alkylamine oxides or N-acylaminopropylmorpholine oxides. It will be noted that the alkylpolyglycosides constitute nonionic surfactants that may be suitable in the context of the present disclosure.

(iii) Amphoteric Surfactant(s):

The amphoteric surfactants, whose nature is not a critical feature in the context of the present disclosure, can be, for example, aliphatic secondary or tertiary amine derivatives wherein the aliphatic radical is a linear or branched chain comprising 8 to 22 carbon atoms and comprising at least one water-soluble anionic group (such as carboxylate, sulfonate, sulfate, phosphate, or phosphonate); non-limiting mention may also be made of ($C_8$-$C_{20}$)alkylbetaines, sulfobetaines, ($C_8$-$C_{20}$)alkylamido($C_1$-$C_6$)alkylbetaines and ($C_8$-$C_{20}$)alkylamido($C_1$-$C_6$)alkylsulfobetaines.

Among the amine derivatives, non-limiting mention may be made of the products sold under the name MIRANOL, as described in U.S. Pat. Nos. 2,528,378 and 2,781,354 and having the structures:

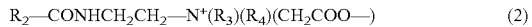

$$R_2\text{—CONHCH}_2\text{CH}_2\text{—N}^+(R_3)(R_4)(\text{CH}_2\text{COO—}) \quad (2)$$

wherein:
- $R_2$ is chosen from alkyl radicals derived from an acid $R_2$—COOH present in hydrolyzed coconut oil, heptyl, nonyl and undecyl radicals, $R_3$ is chosen from β-hydroxyethyl groups and $R_4$ is chosen from carboxymethyl groups; and

$$R_5\text{—CONHCH}_2\text{CH}_2\text{—N(B)(C)} \quad (3)$$

wherein:
- B is chosen from —$CH_2CH_2OX'$, C is chosen from —$(CH_2)_z$—Y', with z=1 or 2,
- X' is chosen from —$CH_2CH_2$—COOH groups and hydrogen, Y' is chosen from —COOH and —$CH_2$—CHOH—$SO_3H$ radicals, $R_5$ is chosen from alkyl radicals of an acid $R_5$—COOH present in coconut oil or in hydrolyzed linseed oil, alkyl radicals, such as a $C_7$, $C_9$, $C_{11}$ or $C_{13}$ alkyl radical, a $C_{17}$ alkyl radical and its iso form, an unsaturated $C_{17}$ radical.

These compounds are classified in the CTFA dictionary, 5th edition, 1993, under the names disodium cocoamphodiacetate, disodium lauroamphodiacetate, disodium caprylamphodiacetate, disodium capryloamphodiacetate, disodium cocoamphodipropionate, disodium lauroamphodipropionate, disodium caprylampho-dipropionate, disodium caryloamphodipropionate, lauroamphodipropionic acid, cocoamphodipropionic acid.

By way of example, non-limiting mention may be made of the cocoamphodiacetate sold under the trade name MIRANOL C2M concentrate by the company Rhône-Poulenc.

(iv) The cationic surfactants may be chosen from:

A) quaternary ammonium salts of formula (IV) below:

wherein:

$X^-$ is an anion chosen from halides (chloride, bromide or iodide) and ($C_2$-$C_6$)alkyl sulfates, such as methyl sulfate, phosphates, alkyl or alkylaryl sulfonates, anions derived from organic acid, such as acetate or lactate, and a) the radicals $R_1$ to $R_3$, which may be identical or different, are chosen from linear or branched aliphatic radicals comprising 1 to 4 carbon atoms, and aromatic radicals such as aryl or alkylaryl. The aliphatic radicals can comprise heteroatoms such as oxygen, nitrogen, sulfur, or halogens. The aliphatic radicals may be chosen, for example, from alkyl, alkoxy and alkylamide radicals, $R_4$ is chosen from linear or branched alkyl radicals comprising 16 to 30 carbon atoms.

The cationic surfactant may, for instance, be a behenyltrimethylammonium salt (such as chloride).

b) the radicals $R_1$ and $R_2$, which may be identical or different, are chosen from linear or branched aliphatic radicals comprising 1 to 4 carbon atoms, and aromatic radicals such as aryl or alkylaryl. The aliphatic radicals may comprise heteroatoms such as oxygen, nitrogen, sulfur, or halogens. The aliphatic radicals are chosen, for example, from alkyl, alkoxy, alkylamide, and hydroxyalkyl radicals comprising 1 to 4 carbon atoms;

$R_3$ and $R_4$, which may be identical or different, are chosen from linear or branched alkyl radicals comprising 12 to 30 carbon atoms, said radicals comprising at least one ester or amide function.

$R_3$ and $R_4$ are chosen, for example, from ($C_{12}$-$C_{22}$)alkylamido($C_2$-$C_6$)alkyl and ($C_{12}$-$C_{22}$)alkylacetate radicals.

The cationic surfactant may, for example, be a stearamidopropyldimethyl(myristyl acetate)ammonium salt (such as chloride).

B) quaternary ammonium salts of imidazolinium, such as, that of formula (V) below:

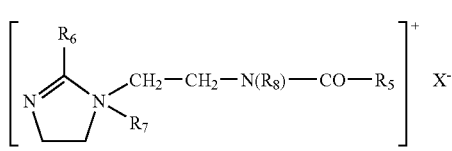 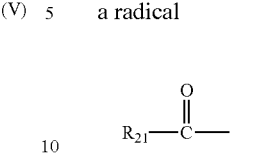

wherein:

$R_5$ is chosen from alkenyl or alkyl radicals comprising 8 to 30 carbon atoms, for example fatty acid derivatives of tallow, $R_6$ is chosen from hydrogen, $C_1$-$C_4$ alkyl radicals and alkenyl or alkyl radicals comprising 8 to 30 carbon atoms, $R_7$ is chosen from $C_1$-$C_4$ alkyl radicals, $R_8$ is chosen from hydrogen and $C_1$-$C_4$ alkyl radicals, and X is an anion chosen from halides, phosphates, acetates, lactates, alkyl sulfates, alkyl sulfonates, and alkylaryl sulfonates.

$R_5$ and $R_6$ may be chosen from, in at least one embodiment, mixtures of alkenyl and alkyl radicals comprising 12 to 21 carbon atoms, such as, fatty acid derivatives of tallow, $R_7$ is methyl and $R_8$ is hydrogen. Such a product is, for example, Quaternium-27 (CTFA 1997) or Quaternium-83 (CTFA 1997), which are sold under the trade names REWOQUAT W75, W90, W75PG and W75HPG by the company Witco, C) diquaternary ammonium salts of formula (VI):

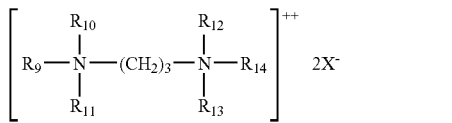 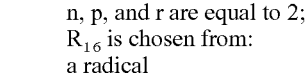

wherein:

$R_9$ is chosen from aliphatic radicals comprising 16 to 30 carbon atoms, $R_{10}$, $R_{11}$, $R_{12}$, $R_{13}$ and $R_{14}$, which may be identical or different, are chosen from hydrogen and alkyl radicals comprising 1 to 4 carbon atoms, and X is an anion chosen from halides, acetates, phosphates, nitrates, and methyl sulfates. Such diquaternary ammonium salts, for example, comprise propanetallowediammonium dichloride.

D) quaternary ammonium salts comprising at least one ester function, of formula (VII) below:

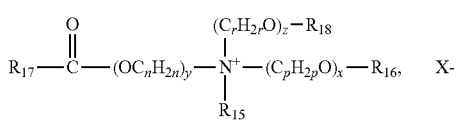

wherein:

$R_{15}$ is chosen from $C_1$-$C_6$ alkyl radicals and $C_1$-$C_6$ hydroxyalkyl and dihydroxyalkyl radicals;

$R_{16}$ is chosen from:

a radical

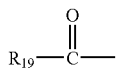

linear or branched, saturated or unsaturated $C_1$-$C_{22}$ hydrocarbon-based radicals $R_{20}$, hydrogen, $R_{18}$ is chosen from:

a radical

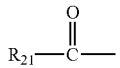

linear or branched, saturated or unsaturated $C_1$-$C_6$ hydrocarbon-based radicals $R_{22}$, hydrogen, $R_{17}$, $R_{19}$ and $R_{21}$, which may be identical or different, are chosen from linear or branched, saturated or unsaturated $C_7$-$C_2$, hydrocarbon-based radicals;

n, p, and r, which may be identical or different, are integers ranging from 2 to 6;

y is an integer ranging from 1 to 10;

x and z, which may be identical or different, are integers ranging from 0 to 10;

$X^-$ is a simple or complex organic or inorganic anion;

with the proviso that the sum x+y+z is from 1 to 15, that when x is 0, then $R_{16}$ is $R_{20}$ and that when z is 0, then $R_{18}$ is $R_{22}$.

In at least one embodiment, use is made, for example, of the ammonium salts of formula (VII) wherein:

$R_{15}$ is chosen from methyl and ethyl radicals, x and y are equal to 1;

z is equal to 0 or 1;

n, p, and r are equal to 2;

$R_{16}$ is chosen from:

a radical

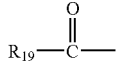

methyl, ethyl, and $C_{14}$-$C_{22}$ hydrocarbon-based radicals, hydrogen;

$R_{17}$, $R_{19}$ and $R_{21}$, which may be identical or different, are chosen from linear or branched, saturated or unsaturated $C_7$-$C_{21}$ hydrocarbon-based radicals;

$R_{18}$ is chosen from:

a radical

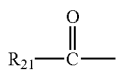

hydrogen.

Such compounds are sold, for example, under the trade name DEHYQUART by the company Henkel, STEPANQUAT by the company Stepan, NOXAMIUM by the company Ceca, and REWOQUAT WE 18 by the company Rewo-Witco.

The composition, as disclosed herein, may comprise quaternary ammonium salts such as behenyltrimethylammonium chloride, or alternatively stearamidopropyldimethyl(myristyl acetate)ammonium chloride, sold, for example, under the name CERAPHYL 70 by the company Van Dyk, Quaternium-27 or Quaternium-83 sold by the company Witco, and dicetearylethyl hydroxyethyl methyl ammonium methosulfate, sold by the company Cognis under the trade name DEHYQUART F75.

The cosmetically acceptable aqueous medium comprises solely water or a mixture of water and of a cosmetically acceptable solvent chosen from $C_1$-$C_4$ lower alcohols, such as ethanol, isopropanol, tert-butanol, or n-butanol; polyols, for instance propylene glycol; polyol ethers; $C_5$-$C_{10}$ alkanes; $C_3$-$C_4$ ketones, for instance acetone and methyl ethyl ketone; $C_1$-$C_4$ alkyl acetates, for instance methyl acetate, ethyl acetate, and butyl acetate; dimethoxyethane or diethoxyethane; and mixtures thereof.

The concentration of cosmetically acceptable solvents other than water (when they are present) may range from 0.1% to 40% by weight and, for instance, from 0.5% to 20% by weight relative to the total weight of the composition.

The composition may comprise from 30% to 99% of water, for instance, from 50% to 95% of water and, further for instance, from 70% to 95% by weight of water relative to the total weight of the composition.

The pH of the compositions of the present disclosure ranges from 4 to 8 and, for example, from 5 to 7.

The composition, as disclosed herein, may also comprise at least one additive chosen from thickeners, fragrances, nacreous agents, preserving agents, vitamins, provitamins, anionic or nonionic polymers, proteins, protein hydrolysates, 18-methyleicosanoic acid, hydroxy acids, provitamins such as panthenol, and any other additive conventionally used in cosmetics that does not affect the properties of the compositions according to the disclosure.

A person skilled in the art will take care to select the optional additives and the amount thereof such that they do not harm the properties of the compositions of the present disclosure.

These additives are optionally present in the composition according to the present disclosure in proportions that may range from 0.001% to 20% by weight relative to the total weight of the composition. The precise amount of each additive is readily determined by a person skilled in the art, depending on its nature and its function.

The compositions in accordance with the present disclosure may be used for caring for and/or treating keratin materials such as the hair, the skin, the eyelashes, the eyebrows, the nails, the lips, and the scalp, for example, the hair.

The compositions according to the present disclosure may be in the form of rinse-out or leave-in hair conditioners, permanent-waving, hair-relaxing, dyeing or bleaching compositions, or in the form of rinse-out compositions, to be applied before or after dyeing, bleaching, permanent-waving, or relaxing the hair or alternatively between the two steps of a permanent-waving or hair-relaxing operation.

According to one embodiment of the present disclosure, the composition may be used as a hair conditioner.

When the composition is in the form of a hair conditioner or of a care composition optionally to be rinsed out, it comprises at least one cationic surfactant, the concentration of which may range from 0.1% to 10% by weight and, for instance, from 0.5% to 5% by weight relative to the total weight of the composition. It may also comprise at least one amphoteric or nonionic surfactant.

Still, another aspect of the present disclosure is a cosmetic process for treating keratin materials such as the skin or the hair, comprising applying to the keratin materials a cosmetic composition, as defined herein, optionally followed by rinsing with water.

Thus, this process according to the present disclosure allows hold of the hairstyle, and treatment or care of the skin, the hair, and any other keratin material, for example the hair.

The compositions according to the present disclosure may also be in the form of aqueous or aqueous-alcoholic lotions for skincare and/or haircare.

The cosmetic compositions according to the present disclosure may be in the form of a gel, a milk, a cream, an emulsion, a thickened lotion, or a mousse and may be used for the skin, the nails, the eyelashes, the lips, and the hair.

The compositions may be conditioned in various forms, such as in jars, bottles, tubes, vaporizers, or pump-dispenser bottles, or in aerosol containers to allow application of the composition in vaporized form or in the form of a mousse. Such conditioning forms are indicated, for example, when it is desired to obtain a spray, a lacquer, or a mousse for treating the hair.

Throughout the text hereinabove and hereinbelow, the percentages are expressed on a weight basis.

Other than in the operating examples, or where otherwise indicated, all numbers expressing quantities of ingredients, reaction conditions, and so forth used in the specification and claims are to be understood as being modified in all instances by the term "about." Accordingly, unless indicated to the contrary, the numerical parameters set forth in the following specification and attached claims are approximations that may vary depending upon the desired properties sought to be obtained by the present disclosure. At the very least, and not as an attempt to limit the application of the doctrine of equivalents to the scope of the claims, each numerical parameter should be construed in light of the number of significant digits and ordinary rounding approaches.

Notwithstanding that the numerical ranges and parameters setting forth the broad scope of the disclosure are approximations, the numerical values set forth in the specific examples are reported as precisely as possible. Any numerical value, however, inherently contain certain errors necessarily resulting from the standard deviation found in their respective testing measurements.

The following examples are intended to illustrate the disclosure in a non-limiting manner. In the examples, the term "AM" is understood to mean active material.

EXAMPLES 1 AND 2

Two hair conditioners in accordance with the present disclosure having the composition below, were prepared:

|  | 1 | 2 | A (comparative) | B (comparative) | C (comparative) |
|---|---|---|---|---|---|
| Pregelatinized corn distarch phosphate (Structure Zea from National Starch) | 0.5 g | 0.2 g | — | — | 2 g |
| PEG-150 distearate (Kessco PEG 6000 DS from Akzo) | 0.5 g | 0.3 g | — | 0.5 g | |

-continued

|  | 1 | 2 | A (comparative) | B (comparative) | C (comparative) |
|---|---|---|---|---|---|
| Polyquaternium-37 (Salcare SC 95 from Ciba-Geigy) | 1 g AM | 1 g AM | 1 g AM | 1 g AM | 1 g AM |
| SMDI/polyethylene glycol copolymer comprising alkyl end groups (methyl/$C_{18}$) at 15% in a maltodextrin/water matrix (Aculyn 46 from Rohm Haas) | 3 g AM | 3 g AM | 3 g AM | 3 g AM | 3 g AM |
| Cetylstearyl alcohol (50/50 by weight) | 8 g | 8 g | 8 g | 8 g | 8 g |
| Cetyl esters: mixture of myristyl/cetyl/stearyl myristate/palmitate/stearate (Miraceti from Laserson) | 1.5 g | 1.5 g | 1.5 g | 1.5 g | 1.5 g |
| Candelilla wax (Candelilla Wax SP 75 from Strahl & Pitsch) | 2 g | 2 g | 2 g | 2 g | 2 g |
| Fragrance, preserving agent | qs | qs | qs | qs | qs |
| Water qs | 100 g | 100 g | 100 g | 100 g | 100 g |

Compositions 1 and 2 had a creamy and very fondant texture when applied to wet hair, while at the same time giving a treating sensory presence on the hair. Compositions 1 and 2 rinsed out easily. The hair was soft and smooth.

Compositions A, B, and C were creamy, but did not lead to the perception of a sufficient treating effect.

EXAMPLE 3

A hair conditioner in accordance with the present disclosure, having the composition below, was prepared:

|  | 3 | D (comparative) | E (comparative) | F (comparative) |
|---|---|---|---|---|
| Pregelatinized corn distarch phosphate (Structure Zea from National Starch) | 0.2 g | — | — | 0.5 g |
| PEG-150 distearate (Kessco PEG 6000 DS from Akzo) | 0.3 g | — | 0.5 g | — |
| Glyceryl stearate (Tegin 6070 from Degussa) | 1 g | 1 g | 1 g | 1 g |
| Cetyltrimethylammonium chloride (Arquad 16-25 LO from Akzo Nobel) | 0.75 g AM | 0.75 g AM | 0.75 g AM | 0.75 g AM |
| Quaternium-80 (Abil Quat 3272 from Degussa) | 0.3 g AM | 0.3 g AM | 0.3 g AM | 0.3 g AM |
| Dipalmitoyl ethyl hydroxyethyl ammonium methosulfate (Dehyquart F75 from Cognis) | 1.7 g AM | 1.7 g AM | 1.7 g AM | 1.7 g AM |
| Cetylstearyl alcohol (50/50 by weight) | 2.8 g | 2.8 g | 2.8 g | 2.8 g |
| Cetyl esters: mixture of myristyl/cetyl/stearyl myristate/palmitate/stearate (Miraceti from Laserson) | 1.5 g | 1.5 g | 1.5 g | 1.5 g |
| Water qs | 100 g | 100 g | 100 g | 100 g |

Composition 3 had a creamy and very fondant texture when applied to wet hair, while at the same time giving a treating sensory presence on the hair. Composition 3 rinsed out easily. The hair was soft and smooth. Compositions D, E, and F were creamy, but did not lead to the perception of a sufficient treating effect.

What is claimed is:

1. A cosmetic composition, in a cosmetically acceptable medium, comprising:
   from 0.1% to 2% by weight, relative to the total weight of the composition, of at least one starch, and
   from 0.1% to 1% by weight, relative to the total weight of the composition, of at least one diester of a carboxylic acid and of polyethylene glycol having the following formula:

$$R_1-CO(O-CH_2-CH_2)n\text{-}OOCR_2 \qquad (I)$$

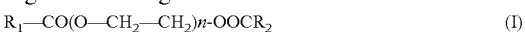

wherein:
   $R_1$ is chosen from linear or branched, saturated or unsaturated alkyl or alkenyl groups comprising 8 to 30 carbon atoms,
   $R_2$ is chosen from linear or branched, saturated or unsaturated alkyl groups comprising 8 to 30 carbon atoms, and
   n is an integer ranging from 80 to 350.

2. A composition according to claim 1, wherein the at least one starch is chosen from corn starch, rice starch, cassava starch, oat starch, tapioca starch, barley starch, potato starch, wheat starch, sorghum starch, and pea starch.

3. A composition according to claim 1, wherein the at least one starch is modified by at least one of the following reactions: pregelatinization, oxidation, crosslinking, esterification, and heat treatments.

4. A composition according to claim 1, wherein the at least one starch is chosen from monostarch phosphates, distarch phosphates and tristarch phosphates, and mixtures thereof.

5. A composition according to claim 1, wherein the at least one starch is chosen from amphoteric starches.

6. A composition according to claim 1, wherein $R_1$ and $R_2$ are chosen from linear alkyl groups comprising 12 to 20 carbon atoms and n ranges from 100 to 300.

7. A composition according to claim 1, wherein the at least one starch is present in an amount ranging from 0.1% to 1% by weight relative to the total weight of the composition.

8. A composition according to claim 1, wherein the at least one diester is present in an amount ranging from 0.1% to less than 0.5% by weight relative to the total weight of the composition.

9. A composition according to claim 1, further comprising at least one agent chosen from plant, animal, mineral or synthetic oils, waxes, ceramides, pseudoceramides, silicones, cationic polymers, surfactants, fatty esters other than diesters of a carboxylic acid comprising 8 to 30 carbon atoms and of polyethylene glycol, sunscreens, and vitamins.

10. A composition according to claim 8, wherein the at least one agent is present in an amount ranging from 0.001% to 20% by weight relative to the total weight of the composition.

11. A composition according to claim 10, wherein the at least one agent is present in an amount ranging from 0.001% to 10% by weight relative to the total weight of the composition.

12. A composition according to claim 1, further comprising at least one surfactant chosen from anionic, nonionic, amphoteric, and cationic surfactants, and mixtures thereof.

13. A composition according to claim 12, wherein the at least one surfactant is chosen from cationic surfactants, and mixtures thereof.

14. A composition according to claim 13, wherein the at least one cationic surfactant is present in an amount ranging from 0.1% to 10% by weight relative to the total weight of the composition.

15. A composition according to claim 14, wherein the at least one cationic surfactant is present in an amount ranging from 0.5% to 5% by weight relative to the total weight of the composition.

16. A composition according to claim 1, wherein the composition is in a form chosen from a hair conditioner, a composition for permanent-waving, relaxing, dyeing or bleaching the hair, and a rinse-out composition to be applied between the two steps of a permanent-waving or a hair-relaxing operation.

17. A process for treating and/or caring for keratin fibers comprising applying to the fibers a cosmetic composition comprising, in a cosmetically acceptable medium:
from 0.1% to 2% by weight, relative to the total weight of the composition, of at least one starch, and
from 0.1% to 1% by weight, relative to the total weight of the composition, of at least one diester of a carboxylic acid and of polyethylene glycol having the following formula:

$$R_1\text{—CO(O—CH}_2\text{—CH}_2)_n\text{-OOCR}_2 \quad (I)$$

wherein:
$R_1$ is chosen from linear or branched, saturated or unsaturated alkyl or alkenyl groups comprising 8 to 30 carbon atoms,
$R_2$ is chosen from linear or branched, saturated or unsaturated alkyl groups comprising 8 to 30 carbon atoms,
n is an integer ranging from 80 to 350.

18. A process according to claim 17, wherein said treating and/or caring for keratin fibers comprises conditioning the hair.

19. A process according to claim 17, said process further comprising, after applying said composition to said fibers, optionally rinsing said fibers with water.

20. A cosmetic composition, in a cosmetically acceptable medium, comprising:
from 0.1% to 2% by weight, relative to the total weight of the composition, of at least one amphoteric starch chosen from monostarch phosphates, distarch phosphates and tristarch phosphates, and mixtures thereof, and
from 0.1% to 1% by weight, relative to the total weight of the composition, of at least one diester of a carboxylic acid and of polyethylene glycol having the following formula:

$$R_1\text{—CO(O—CH}_2\text{—CH}_2)_n\text{-OOCR}_2 \quad (I)$$

wherein:
$R_1$ is chosen from linear or branched, saturated or unsaturated alkyl or alkenyl groups comprising 8 to 30 carbon atoms,
$R_2$ is chosen from linear or branched, saturated or unsaturated alkyl groups comprising 8 to 30 carbon atoms, and
n is an integer ranging from 80 to 350.

* * * * *